US00PP19648P2

(12) United States Plant Patent
Maas

(10) Patent No.: US PP19,648 P2
(45) Date of Patent: Jan. 20, 2009

(54) ***VERBASCUM* PLANT NAMED 'FLOWER OF SCOTLAND'**

(50) Latin Name: *Verbascum hybrida*
Varietal Denomination: Flower of Scotland

(76) Inventor: Dick Maas, 3e Loosterweg 130, 2182 CX Hillegom (NL)

( * ) Notice: Subject to any disclaimer, the term of this patent is extended or adjusted under 35 U.S.C. 154(b) by 209 days.

(21) Appl. No.: 11/483,248

(22) Filed: Jul. 7, 2006

(51) Int. Cl.
*A01H 5/00* (2006.01)

(52) U.S. Cl. ..... Plt./489

(58) Field of Classification Search ..... Plt./489
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Verbascum* plant named 'Flower of Scotland', characterized by its compact and upright plant habit; medium green-colored foliage; unique greyed purple to greyed red-colored flowers; and good garden performance.

1 Drawing Sheet

Botanical designation: *Verbascum hybrida.*
Cultivar denomination: 'Flower of Scotland'.

BACKGROUND OF THE INVENTION

The present invention relates to a new and distinct cultivar of *Verbascum,* botanically known as *Verbascum hybrida* and hereinafter referred to by the name 'Flower of Scotland'.

The new *Verbascum* is a naturally-occurring whole plant mutation of an unnamed selection of *Verbascum hybrida,* not patented.

The new *Verbascum* was discovered by the Inventor in a controlled environment in Gretna Green, Scotland in 1999.

Asexual reproduction of the new *Verbascum* by tissue culture in a controlled environment in Dievers, The Netherlands since 2002, has shown that the unique features of this new *Verbascum* are stable and reproduced true to type in successive generations.

SUMMARY OF THE INVENTION

The cultivar Flower of Scotland has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Flower of Scotland'. These characteristics in combination distinguish 'Flower of Scotland' as a new and distinct cultivar of *Verbascum:*

1. Compact and upright plant habit.
2. Medium green-colored foliage.
3. Unique greyed purple to greyed red-colored flowers.
4. Good garden performance.

Plants of the new *Verbascum* differ from plants of the parent selection in the following characteristics:

1. Plants of the new *Verbascum* are more compact than plants of the parent selection.
2. Plants of the new *Verbascum* and the parent selection differ in plant growth habit.

3. Plants of the new *Verbascum* and the parent selection differ in flower color.

Plants of the new *Verbascum* can be compared to plants of the cultivar Buttercup, disclosed in U.S. Plant Pat. No. 14,793. Plants of the new *Verbascum* and the cultivar Buttercup differ in the following characteristics:

1. Plants of the new *Verbascum* are more compact than plants of the cultivar Buttercup.
2. Plants of the new *Verbascum* and the cultivar Buttercup differ in plant growth habit.
3. Plants of the new *Verbascum* and the cultivar Buttercup differ in flower color.

BRIEF DESCRIPTION OF THE PHOTOGRAPH

The accompanying colored photograph illustrates the overall appearance of the new *Verbascum,* showing the colors as true as it is reasonably possible to obtain in colored reproductions of this type. Colors in the photograph may differ slightly from the color values cited in the detailed botanical description which accurately describe the colors of the new *Verbascum.* The photograph comprises a side perspective view of a typical flowering plant of 'Flower of Scotland' grown in an outdoor nursery.

DETAILED BOTANICAL DESCRIPTION

The aforementioned photograph and following observations, measurements and values describe plants grown in Hiliegom, The Netherlands, under commercial practice during the summer in an outdoor nursery with day temperatures ranging from 14° C. to 33° C. and night temperatures ranging from 7° C. to 18° C. Plants had been growing for about two years when the photograph and description were taken. In the following description, color references are made to The Royal Horticultural Society Colour Chart, 2001 Edition, except where general terms of ordinary dictionary significance are used.

Botanical classification: *Verbascum hybrida* cultivar Flower of Scotland.

Parentage: Naturally-occurring whole plant mutation of an unnamed selection of *Verbascum hybrida,* not patented.

Propagation:

*Type.*—By tissue culture.

*Time to initiate roots.*—About one month at 14° C.

*Root description.*—Thin, fleshy; grey in color.

Plant description:

*Plant form/habit.*—Herbaceous perennial. Compact and upright plant habit; broad inverted triangle; low vigor. Freely basally branching habit, about seven basal flowering stems per plant.

*Plant height.*—About 16 cm.

*Plant width* (*spread*).—About 18.3 cm.

*Flowering stems.*—Length (soil level to base of inflorescence): About 5.5 cm. Diameter: About 2.5 mm. Internode length: About 9 mm. Strength: Strong. Texture: Sparsely pubescent. Color: 144A.

Foliage description:

*Arrangement.*—Alternate, simple.

*Length.*—About 4.4 cm.

*Width.*—About 1.9 cm.

*Shape.*—Ovate.

*Apex.*—Acute.

*Base.*—Rounded to attenuate.

*Margin.*—Crenate.

*Texture, upper surface.*—Smooth, glabrous.

*Texture, lower surface.*—Sparsely pubescent.

*Venation pattern.*—Pinnate.

*Color.*—Developing leaves, upper surface: 137A. Developing leaves, lower surface: 137B. Fully expanded leaves, upper surface: 137A; venation, 143A to 143B. Fully expanded leaves, lower surface: 137C; venation, 145A.

*Petiole.*—Length: About 2.6 cm. Diameter: About 1.5 mm. Color: 144A to 144B.

Flower description:

*Flower type/habit.*—Single rotate flowers arranged in terminal racemes; flowers face upright to outward. Freely flowering habit with about 250 flower buds and flowers developing per plant.

*Fragrance.*—None detected.

*Natural flowering season.*—Continuously flowering throughout the summer in The Netherlands. Flowers not persistent.

*Postproduction longevity.*—Flowers last about five days on the plant.

*Flower buds.*—Height: About 5 mm. Diameter: About 6 mm. Shape: Flattened orbicular. Color: 183B.

*Inflorescence height.*—About 6.7 cm.

*Inflorescence diameter.*—About 7.2 cm.

*Flower diameter.*—About 2.6 cm.

*Flower depth.*—About 9 mm.

*Petals.*—Quantity per flower: Typically five in a single whorl; petals fused at the base. Length: About 1.3 cm. Width: About 1.4 cm. Shape: Orbicular. Apex: Rounded. Margin: Entire. Texture, upper and lower surfaces: Smooth, glabrous. Color: When opening, upper surface: 182C. When opening, lower surface: 182D. Fully opened, upper and lower surfaces: 185D; color becoming closer to 182A with development.

*Sepals.*—Quantity per flower: Typically five in a single whorl. Length: About 5 mm. Width: About 2.5 mm. Shape: Elliptic. Apex: Acute. Base: Cuneate. Margin: Entire. Texture, upper surface: Smooth, glabrous. Texture, lower surface: Densely pubescent. Color: When opening, upper surface: 141B. When opening, lower surface: 141B to 141C. Fully opened, upper and lower surfaces: 141B.

*Peduncles.*—Length: About 6.7 cm. Diameter: About 3 mm. Angle: About 25° from vertical. Strength: Strong. Texture: Smooth, glabrous. Color: 144A.

*Pedicels.*—Length: About 2.6 cm. Diameter: About 1 mm. Angle: About 80° from vertical. Strength: Strong. Texture: Smooth, glabrous. Color: 143B.

*Reproductive organs.*—Stamens: Quantity per flower: Typically five. Filament length: About 6 mm. Filament color: 17B. Anther shape: Broadly triangular. Anther length: About 2 mm. Anther color: 183A. Pollen amount: Scarce. Pollen color: 17C to 17D. Pistils: Quantity per flower: One. Pistil length: About 9 mm. Stigma shape: Club-shaped. Stigma color: 144B. Style length: About 8 mm. Style color: 144A. Ovary color: 145A.

*Seed/fruit.*—Seed and fruit development have not been observed.

Disease/pest resistance: Plants of the new *Verbascum* have not been noted to be resistant to pathogens and pests common to *Verbascum.*

Garden performance: Plants of the new *Verbascum* have been observed to have good garden performance and tolerate rain, wind and are winter hardy in The Netherlands.

It is claimed:

1. A new and distinct *Verbascum* plant named 'Flower of Scotland' as illustrated and described.

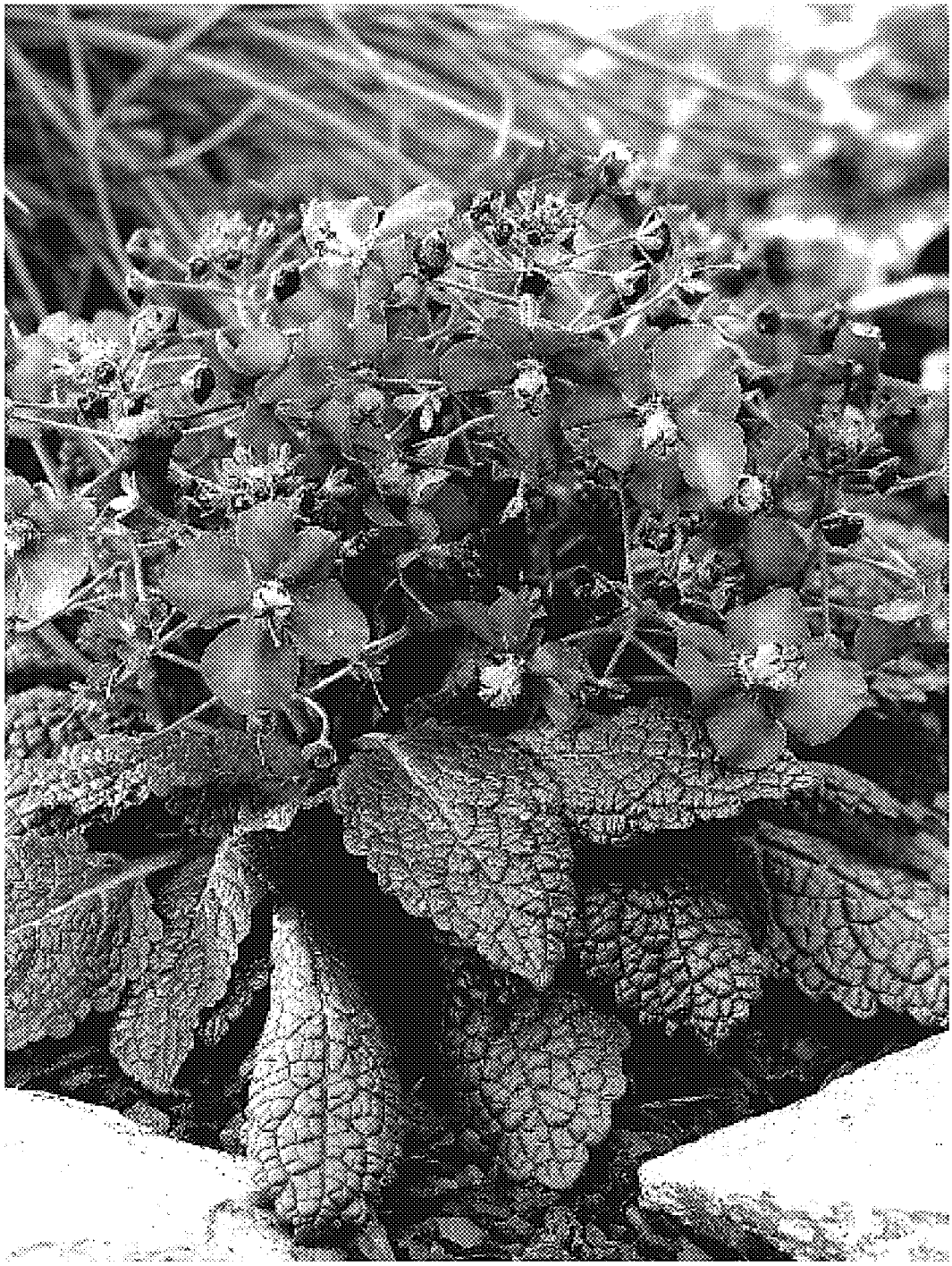

* * * * *